United States Patent

Segawa

[11] Patent Number: 5,865,177
[45] Date of Patent: Feb. 2, 1999

[54] MAGNETIC RESONANCE IMAGING (MRI) DIAGNOSTIC APPARATUS CAPABLE OF OPTIMALLY CONTROLLING RADIO-FREQUENCY MAGNETIC FIELD BY PROVIDING FLEXIBLE MATERIAL INTERPOSED BETWEEN RF COIL AND BODY

[75] Inventor: Toru Segawa, Tochigiken, Japan

[73] Assignee: Kabushiki Kaisha Toshiba, Kawasaki, Japan

[21] Appl. No.: 590,619

[22] Filed: Jan. 24, 1996

Related U.S. Application Data

[63] Continuation of Ser. No. 261,394, Jun. 17, 1994, abandoned.

[30] Foreign Application Priority Data

Jun. 24, 1993 [JP] Japan .................................... 5-153148

[51] Int. Cl.⁶ .................................................... A61B 5/055
[52] U.S. Cl. ........................................ 128/653.2; 324/318
[58] Field of Search .............................. 128/653.2, 653.5; 324/318, 322

[56] References Cited

U.S. PATENT DOCUMENTS

| 5,227,727 | 7/1993 | Segawa et al. ......................... 324/318 |
| 5,280,248 | 1/1994 | Zou et al. ............................. 128/653.5 |

OTHER PUBLICATIONS

SMRM Abstracts, Vol. 1, pg. 510; Thomas K.F. Foo et al.; 1990

*Primary Examiner*—Ruth S. Smith
*Attorney, Agent, or Firm*—Limbach & Limbach LLP; Ronald L. Yin

[57] ABSTRACT

A magnetic resonance imaging (MRI) diagnostic apparatus capable of eliminating density inhomogeneity of the tomographic images obtained thereby. The MRI diagnostic apparatus includes a gantry for defining a space for a MRI diagnosis; an RF shield, disposed inside the gantry and outside an RF coil; and material for correcting a distribution of an RF magnetic field at the time of RF transmitting or receiving by the RF coil, wherein the field correcting material is interposed between the biological body lying inside the shield and the RF coil. Preferably, the field correcting material includes an aqueous high-molecular gel sheet which is flexibly deformable along the shape of the biological body.

5 Claims, 7 Drawing Sheets

$$\rho = -\nabla \cdot P \quad \textit{FIG. 16-a} \qquad j = \frac{\partial P}{\partial t} \quad \textit{FIG. 16-b}$$

$$\nabla \cdot E = \frac{\nabla \cdot P}{\varepsilon_0} \quad \textit{FIG. 16-c} \qquad c^2 \nabla \times B = \frac{\partial}{\partial t}\left(\frac{P}{\varepsilon_0} + E\right) \quad \textit{FIG. 16-d}$$

$$\nabla \times E = \frac{\partial B}{\partial t} \quad \textit{FIG. 16-e} \qquad \nabla \cdot B = 0 \quad \textit{FIG. 16-f}$$

$$\nabla(\nabla \times E) = -\frac{\partial}{\partial t}\nabla \times B \quad \textit{FIG. 16-g}$$

$$\nabla(\nabla \cdot E) - \nabla^2 E = -\frac{1}{\varepsilon_0 c^2}\frac{\partial^2 P}{\partial t^2} - \frac{1}{c^2}\frac{\partial^2 E}{\partial t^2} \quad \textit{FIG. 16-h}$$

$$\nabla^2 E - \frac{1}{c^2}\frac{\partial^2 E}{\partial t^2} = -\frac{1}{\varepsilon_0}\nabla(\nabla \cdot P) + \frac{1}{\varepsilon_0 c^2}\frac{\partial^2 P}{\partial t^2} \quad \textit{FIG. 16-i}$$

$$E_x = E_0 e^{i(\omega t - kz)} = E_0 e^{-ik\left(z - \frac{\omega}{k}t\right)} \quad \textit{FIG. 16-j}$$

$$\left\{\frac{\partial^2 P_x}{\partial t^2} = \omega^2 P_x \quad \frac{\partial^2 E_x}{\partial z^2} = -k^2 E_x\right\} \quad \textit{FIG. 16-k}$$

$$-k^2 E_x + \frac{\omega^2}{c^2} E_x = -\frac{\omega^2}{\varepsilon_0 c^2} P_x \quad \textit{FIG. 16-l}$$

$$k^2 = \frac{\omega^2}{c^2}(1 + N\alpha) \quad \textit{FIG. 16-m} \qquad n^2 = 1 + N\alpha \quad \textit{FIG. 16-n}$$

$$n^2 = 1 + \frac{N\alpha}{1 - (N\alpha/3)} \quad \textit{FIG. 16-o} \qquad 3\frac{n^2 - 1}{n^2 + 2} = N\alpha \quad \textit{FIG. 16-p}$$

$$3\left(\frac{n^2 - 1}{n^2 + 2}\right) = \alpha \sum_j N_j \alpha_j \quad \textit{FIG. 16-q}$$

$$3\left(\frac{n^2 - 1}{n^2 + 2}\right) = \frac{Nq_e^2}{m\varepsilon_0} \sum_k \frac{f_k}{-\omega^2 + i\gamma_k \omega + \omega_{0k}^2} \quad \textit{FIG. 16-r}$$

$$\begin{cases} E_i = E_0 e^{i(\omega t - k_x x - k_y y)} \\ E_r = E_0' e^{i(\omega' t - k_x' x - k_y' y)} \\ E_t = E_0'' e^{i(\omega'' t - k_x'' x - k_y'' y)} \end{cases}$$ FIG. 16-s $$\begin{cases} B_i = \dfrac{k_x E_i}{\omega} \\ B_r = \dfrac{k_x' E_r}{\omega} \\ B_t = \dfrac{k_x' E_t}{\omega} \end{cases}$$ FIG. 16-t $E_0 e^{i(\omega t - k_y y)} + E_0' e^{i(\omega' t - k_y' y)} = E_0'' e^{i(\omega'' t - k_y'' y)}$  FIG. 16-u $E_0 e^{i\omega t} + E_0' e^{i\omega' t} = E_0'' e^{i\omega'' t}$  FIG. 16-v $\dfrac{k''^2}{n_2^2} = \dfrac{k'^2}{n_1^2} = \dfrac{k^2}{n_1^2}$  FIG. 16-w $E_0 e^{-i k_y y} + E_0' e^{-i k_y' y} = E_0'' e^{-i k_y'' y}$  FIG. 16-x $k_y = k_y' = k_y''$  FIG. 16-y $k_x'^2 + k_y'^2 = k_x^2 + k_y^2$  FIG. 16-z $k_x'^2 = k_x^2 \quad (k_x' = \pm k_x)$  FIG. 16-aa $k_x' = -k_x$  FIG. 16-ab $E_r = E_0' e^{i(\omega t - k_x x + k_y y)}$  FIG. 16-ac $\left\{ k_y'' = k_y \text{ ----- and } \dfrac{k''^2}{n_2} = \dfrac{k^2}{n_1^2} \right\}$  FIG. 16-ad $k_x''^2 = k''^2 - k_y''^2 = \dfrac{n_2^2}{n_1^2} k^2 - k_y^2$  FIG. 16-ae

MAGNETIC RESONANCE IMAGING (MRI) DIAGNOSTIC APPARATUS CAPABLE OF OPTIMALLY CONTROLLING RADIO-FREQUENCY MAGNETIC FIELD BY PROVIDING FLEXIBLE MATERIAL INTERPOSED BETWEEN RF COIL AND BODY

This is a continuation of application Ser. No. 08/261,394 filed on Jun. 17, 1994, Now abandoned.

BACKGROUND OF THE INVENTION

1. Technical Field

The present invention relates to a magnetic resonance imaging (MRI) apparatus in which an arbitrary tomographic image is obtained utilizing a nuclear magnetic resonance (NMR) phenomenon, and it particularly relates to the MRI apparatus by which an image quality therefor is improved.

2. Background Art

In recent years of a medical diagnostic apparatus being progressively developed, a magnetic resonance imaging (MRI) apparatus has been widely used. When a tomographic image of a biological body to be examined is imaged by the MRI apparatus, brightness of the tomographic image obtained by the MRI apparatus is generally not uniform even when the body is made of homogeneous material. This nonuniformity is often called a density inhomogeneity. A primary reason for the occurrence of the density inhomogeneity is nonuniformity of the high-frequency magnetic field (RF field inhomogeneity) generated by a radiofrequency (RF) coil. Due to the difference in the shape of the conductive pattern of the RF coil and the distribution of electric current flowing through the conductive pattern of the RF coil, both intensity and direction of transmit-receive sensitivity caused by the RF coil differ in three-dimensional spatial position. In other words, a high-frequency magnetic field vector (RF magnetic field vector) differs at each position.

Now, when the RF magnetic field produced by the RF coil is inhomogeneous in a space where there is placed the biological body to be examined, the magnetic field generated by a transmitting coil is spatially inhomogeneous. Thus, the RF magnetic field vector differs at each location inside the biological body. As a result, a flip angle differs at each location, where the flip angle indicates an amount of rotation of macroscopic magnetization vector produced by an RF pulse with respect to the direction of a static magnetic field.

Therefore, this non-uniform spatial distribution of the RF magnetic field vector intensity directly reflects on the intensity of receive signals. Accordingly, the inhomogeneity in the signal intensity is caused.

As another reason for the density inhomogeneity, there is a state in which the RF magnetic field is propagated in the biological body. This is due to a change in electromagnetic wave caused by interaction between the biological body and the electromagnetic wave. More specifically, the density inhomogeneity is caused by many factors, such as the dielectric constant (relative permittivity) and conductivity of the biological body, and distribution therefor and the boundary conditions determined by the shape of the biological body itself.

As for a general characteristic in the electromagnetic wave, energy thereof is consumed due to an eddy current generated in conductive material when the electromagnetic wave passes through the conductive material. Then, the wavelength thereof varies and there occurs a reflection of the wave due to the dielectric constant. That is, there occurs the reflection or refraction. These phenomena are also caused by the shape of the biological body. Owing to these above described compound effects, the RF magnetic field distribution inside the biological body becomes inhomogeneous depending on the shape, dielectric constant and conductivity of the body, even if the RF coil used produces a uniform (homogeneous) RF magnetic field. The unevenness of the brightness and darkness in the MRI images worsens as the magnitude of the static magnetic field becomes greater and as the Larmor frequency becomes high. Here, the Larmor frequency corresponds to a resonant frequency $\omega_o$ defined by the Larmor equation $$\omega_o = 2\pi f_o.$$

In order to suppress the density nonuniformity (inhomogeneity), there have been proposed the following methods in the conventional practice.

When the uniformity of the RF magnetic field produced by the RF coil is not sufficiently obtained, the brightness of the material which is homogeneous on the image is made uniform by controlling a high-frequency power (RF power) of the transmitter RF coil. For example, in a case of imaging a fat layer of the stomach, even though the fat layer is of the same homogeneous material, there occurs a case where some portion of the fat layer is bright while another is dark. Thus, in order to alleviate this disadvantage, the power supplied to the transmitter coil is controlled. However, since the power is controlled, there is a strong chance that the quality of a thus obtained image is deteriorated. In other words, in this method, only the control concerning the RF magnetic field for the transmitter RF coil is performed while no control is carried out at the time of receiving such data by the receive coil.

As another conventional method, it is considered that a spatial distribution of the electromagnetic field of the RF coil is changed by varying the capacitance of distributed capacitors provided in a wire pattern of the RF coil (receive coil). However, in reality, it is difficult to change the capacitance distribution. Moreover, there can not be obtained a desirable effect by so doing.

SUMMARY OF THE INVENTION

In view of the foregoing drawbacks, it is therefore an object of the present invention to provide a magnetic resonance imaging diagnostic apparatus capable of easily and precisely suppressing the density inhomogeneity of the tomographic images obtained thereby.

To achieve the object, there is provided a magnetic resonance imaging (MRI) diagnostic apparatus in which a radiofrequency (RF) pulse is applied from a RF coil to a biological body, and acquired nuclear magnetic resonance (NMR) signals therefrom is reconstructed so as to obtain an MRI image, the apparatus comprising: a gantry for defining a space for a MRI diagnosis; an RF shield, disposed inside the gantry and outside the RF coil; and means for correcting a distribution of an RF magnetic field at the time of RF transmitting or receiving by the RF coil, wherein the field correcting means is interposed between the biological lying inside the shield and the RF coil.

Alternatively, the field correcting means is provided on a part of or around the entire RF coil.

Preferably, the field correcting means includes an aqueous high-molecular gel sheet which is flexibly deformable along the shape of the biological body.

An advantage of the present invention is that the spatial distribution of the RF magnetic field is optimally controlled to be stabilized so that the image density inhomogeneity is significantly suppressed.

BRIEF DESCRIPTION OF THE DRAWINGS

These and other objects, features and advantages of the present invention will become more apparent from the following description of the preferred embodiment taken in conjunction with the accompanying drawings, in which:

FIGS. 16-*a* through 16-*ae* list equations in explanation of the theoretical analysis for the present invention.

DETAILED DESCRIPTION OF THE PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

BASIC CONFIGURATION

Figure 5:
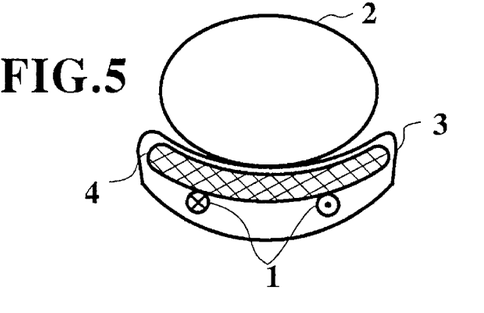
FIG. 5 is a cross sectional view illustrating configuration for regulating an RF magnetic field in MRI diagnostic apparatus according to the first embodiment of the present invention.

FIG. 5 illustrates a configuration for regulating an RF magnetic field in a magnetic resonance imaging (MRI) diagnostic apparatus according to the first embodiment of the present invention.

In FIG. 5, there is provided a sheet 4 filled with an aqueous high-molecular gel, in order to correct the high-frequency magnetic field (radiofrequency (RF) magnetic field) produced by an RF coil 1 in a magnetic resonance imaging (MRI) diagnostic apparatus and to optimally control detection capability for receiving a nuclear magnetic resonance (NMR) signal outputted from a biological body 2 under medical examination. In FIG. 5, a mat 3 includes therein the RF coils 1, 1 and the sheet 4. The aqueous high-molecular gel sheet 4 is placed between the RF coil 1 and the biological body 2.

Figure 6:
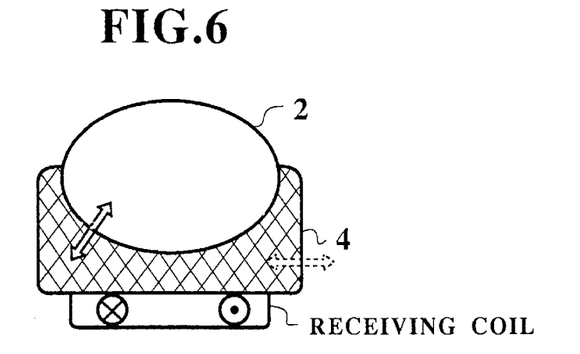
FIG. 6 is an cross sectional view illustrating configuration for regulating the RF magnetic field in the MRI diagnostic apparatus according to the second embodiment.
Figure 7:
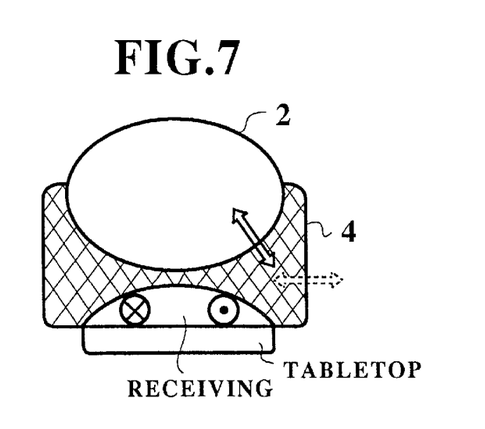
FIG. 7 shows another example for the second embodiment shown in FIG. 6.

In FIG. 6, the aqueous high-molecular gel sheet 4 whose shape can be freely deformable according to the weight of the biological body as it is of flexible material, is attached in contact with the biological body, according to the second embodiment of the present invention. FIG. 7 show a variation of the second embodiment where the shape of the RF coil is different from the one shown in FIG. 6.

In the second embodiment, even though the shape of the biological body varies, the gel sheet 4 having flexibility can also change its shape freely so as to be in direct contact with the body. Since the flexible gel sheet 4 is in direct contact with an almost whole body area, the distribution of the RF magnetic field can be changed so as to produce homogeneous MRI images.

In contrast, in the first embodiment, the gel sheet 4 is already filled in the mat 3, so that the first embodiment is advantageous in that the distribution of the RF magnetic field can be locally changed.

It is to be noted that the magnetization of the biological body differs from that of an air layer surrounding the body. The magnitude of the magnetization is abruptly and greatly changed in a boundary area between the body and the air layer. Thus, in the vicinity of the boundary area the static field is disturbed. More specifically, the vector of the static field or the static field plus a gradient field is disturbed.

Therefore, by filling a space between the RF coil and the body with the gel sheet 4 according to the present invention, the magnetic field, such as the static field, is stabilized.

In other words, referring to FIG. 6 and FIG. 7, the magnetization is not distorted in a region of interest such as one illustrated as the solid arrowmark, while the magnetization is distorted in an area excluding the region of interest, such as one illustrated in the dotted arrowmark.

Accordingly, the gel sheet 4 serves as a matching layer interposed between the biological body and the RF coil.

There may be utilized a poly acryl resin (PAR), a poly vinyl alcohol (PVA) or the like for the aqueous high-molecular gel sheet 4. Morever, the shape for the gel sheet 4 can change according to the shape of the biological body to be examined.

Moreover, there also can be used the liquid having a large permittivity, such as water, and magnetization close to the biological body.

It is preferable that field correcting material such as the aqueous high-molecular gel sheet has a dielectric constant of greater than 30.

Moreover, the magnetization (magnetic susceptibility) of the field correcting material is preferably within approximately ±150% of that of the biological body.

Accordingly, by providing the aqueous high-molecular gel sheet 4 between the biological body and the RF coil as described above, the spatial distribution of the RF magnetic field is optimally controlled. Theoretical explanation therefor is given in the following THEORETICAL ANALYSIS.

Recently, a high-speed imaging technology such as a Fast Spin Echo imaging has been developed. Accompanied by the development in this technique, the heating caused by the RF wave can not be accepted. In other words, there is a strong possibility in the near future that the MRI imaging will be held under a condition where a Specific Absorption Ratio (SAR) is large. In that instance, by employing the present invention where the gel or a liquid bag is provided in contact with the biological body, a heat-radiating efficiency from the biological body is desirable so that the heating of the biological body is suppressed.

Moreover, an operational aspect for the present invention will be discussed in the following section entitled OPERATIVE ASPECT OF THE CONFIGURATION ACHIEVED BY THE PRESENT INVENTION.

VARIATIONS TO THE BASIC CONFIGURATION

Figure 14:
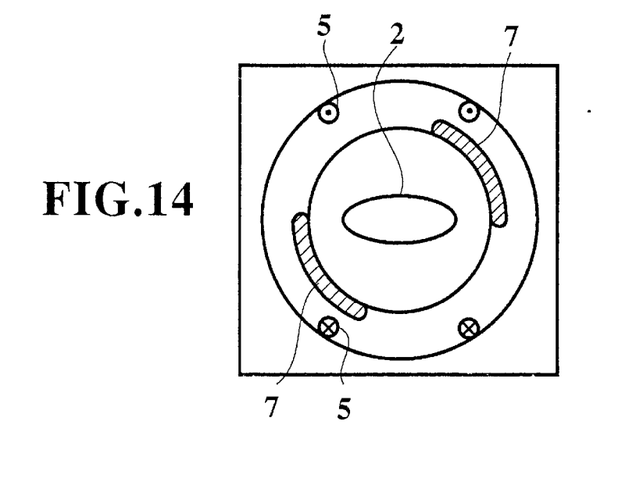

FIG. 14 is a sectional view; showing still other variation for the present invention.

Figure 12:
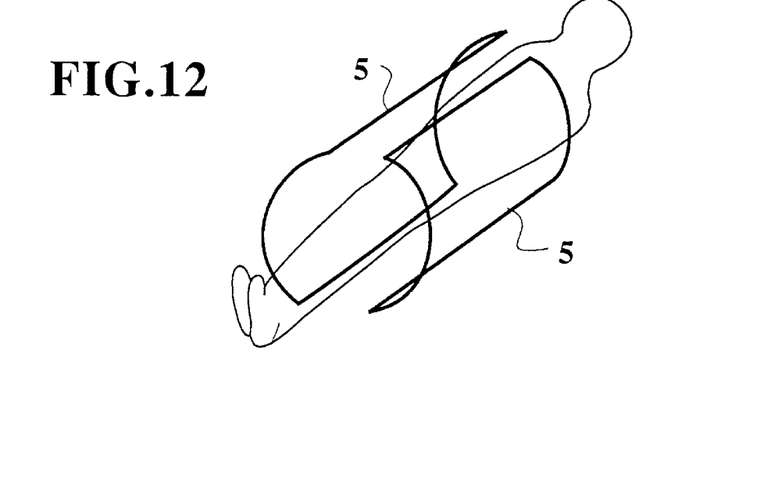
FIG. 12 is a saddle-type coil 5 for describing the variation showing in FIG. 13 and FIG. 14.

In these variations, there is provided the aqueous high-molecular gel sheet in a part of the coil, in order to correct the inhomogeneity of the RF magnetic field existing in the coil itself and to correct the boundary condition determined by the wavelength of the RF magnetic field in the body and the shape of the body placed inside a saddle-type coil 5 shown in FIG. 12.

Thereby, the spatial distribution of the RF magnetic field in the vicinity of the gel sheet, especially a radial-direction component of the RF magnetic field is greatly changed, so that the MRI image is corrected to display a homogeneous image which should be as such.

Figure 13:
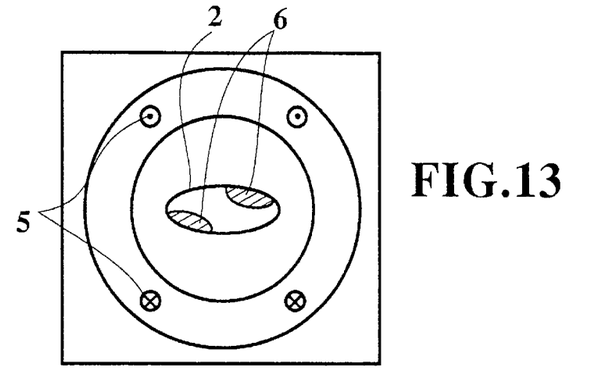
FIG. 13 and FIG. 14 are sectional views showing still other variations for the present invention.

More specifically, referring to FIG. 13 and FIG. 14, when a hatched portion 6 in FIG. 13 becomes dark in the tomographic image of the biological body 2, the dark portion 6 is suppressed so as to correct the density inhomogeneity by providing the high-molecular gel sheet 7 in parts of the coil as shown in FIG. 14.

Figure 15:
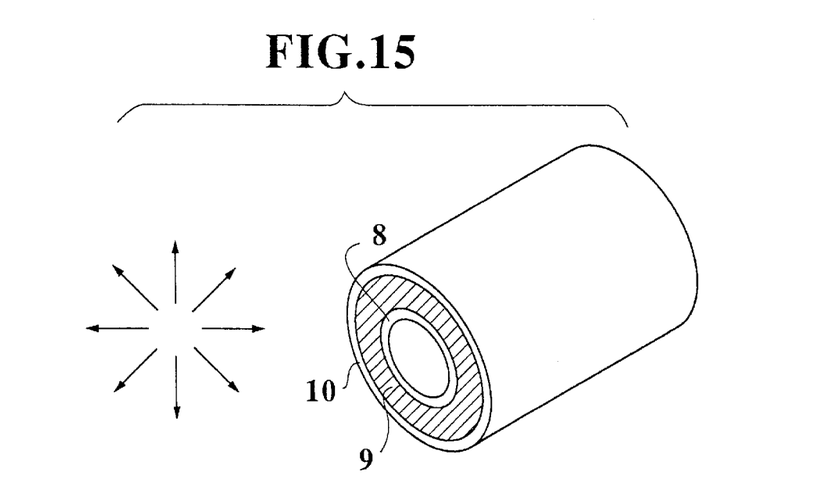
FIG. 15 is a perspective view showing still another variation of the present invention.

FIG. 15 is a perspective view showing still another variation of the present invention. In the same figure, there is provided the aqueous high-molecular gel sheet 9 partially or entirely between the RF coil 8 and an RF shield 10. Here, the RF shield is provided inside the gantry (not shown) and prevents the RF magnetic field from being emanated externally therefrom.

Thereby, the wavelength (which enters into the body) in the radial direction of the RF magnetic field is made longer, so that the density inhomogeneity of the tomographic image of the body can be significantly suppressed.

The above variation where there is provided the gel sheet between the RF coil and the RF shield, may be employed in combination with the above described first embodiment or the second embodiment.

THEORETICAL ANALYSIS

Theoretical explanation for obtaining the above-described superior effects is presented hereinafter.

Please refer to FIGS. 16-$a$ through 16-$ae$ for listing of equations used in the following description.

Figure 16:
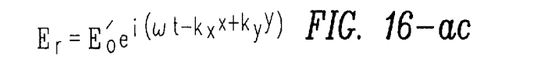
Figure 16S:
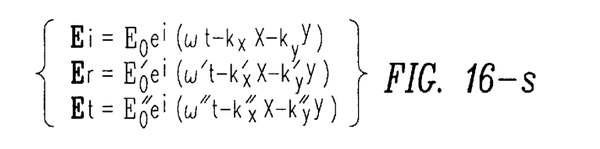
Figure 16T:
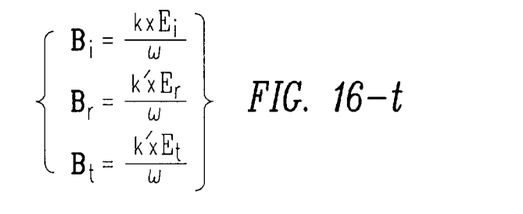
Figure 16U:
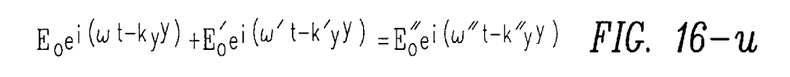

Assuming, for a wave in a dielectric substance, that there are no other currents and charges in the material, except for the charge bounded by the atom, the equations set forth in FIGS. 16-$a$ and 16-$b$ hold, where p indicates a charge density; P is a polarization vector; and j is a current density.

If electromagnetic waves can exist in the dielectric material in which there is no extra charge other than those bound in atoms, then, Maxwell's equations become the equations shown in FIGS. 16-$c$ through 16-$e$, where E represents an electric field vector and B is a magnetic field vector. The $c^2$ represents a square of the velocity of light. Note that $\epsilon_o$ indicates the permittivity of a free space.

Next, by taking the curl of equation shown in FIG. 16-$e$, there is obtained the equation shown in FIG. 16-$a$.

Next, we make use of the vector identity $$\nabla \times (\nabla \times E) = \nabla(\nabla \cdot E) - \nabla^2 E$$

and substitute for $\nabla \times B$, using the equation shown in FIG. 16-$d$, to obtain the equation shown in FIG. 16-$b$.

Using the equation shown in FIG. 16-$c$ for $\nabla \cdot E$, there is obtained the equation shown in FIG. 16-$i$.

Now, let us limit the case to isotropic dielectrics, so that P is in the same direction as E, such that P=αE. When finding a solution for a wave going in the z-direction, the electric field might vary as $e^{i(\omega t - kz)}$. Let us also suppose that the wave is polarized in the x-direction, so that the electric field has only an x-component. Then, there is obtained the equation shown in FIG. 16-$i$. It is to be noted that any function of (z−vt) represents a wave that travels with the speed v.

Therefore, equation (10) represents a wave with a phase velocity $V_{ph}=\omega/k$ where $\omega$ is an angular frequency.

The index of refraction n is defined by using $V_{ph}=c/n$

Thus, the equation shown in FIG. 16-$j$ becomes $E_x = E_o e^{i\omega(t-nz/c)}$

Notice that n=kc/ω.

In an isotropic material, there will be only an x-component of the polarization, then P has no variation with the x-coordinate, so $\nabla \cdot P = 0$. Then, we get rid of the first term on the right-hand side of the equation shown in FIG. 16-$i$. Moreover, in a case of the linear dielectric, the equations shown in FIG. 16-$k$ hold, so that the equation shown in FIG. 16-$k$ becomes the equation shown in 16-$l$.

Now, if assumed that vector E is varying sinusoidally and $P_x = \epsilon_o N\alpha E_x$, term $E_x$ drops out of the equation shown in FIG. 16-$i$. Thus, there is obtained the equation shown in FIG. 16-$m$.

A wave as in the equation shown in FIG. 16-$j$ with the wave number k given by the equation shown in FIG. 16-$m$ will satisfy the field equations. Using equation n=kc/ω, the index n is given by the equation shown in FIG. 16-$n$.

In the dense materials, the equation shown in FIG. 16-$o$ is held, and the equation shown in FIG. 16-$o$ can be rewritten as the equation shown in FIG. 16-p. The equation shown in FIG. 16-$p$ is known as the Clausius-Mosotti equation. Now, defining $N_j$ as being the number of atoms of each component per unit volume, there can be obtained the equation shown in FIG. 16-$q$. This the equation shown in FIG. 16-$q$ can be expressed approximately by the equation shown in FIG. 16-$r$. In the equation shown in FIG. 16-$r$, $\gamma_k$ is the k-th attenuation constant, and $\omega_{ok}$ is the k-th Larmor frequency.

Figure 8:
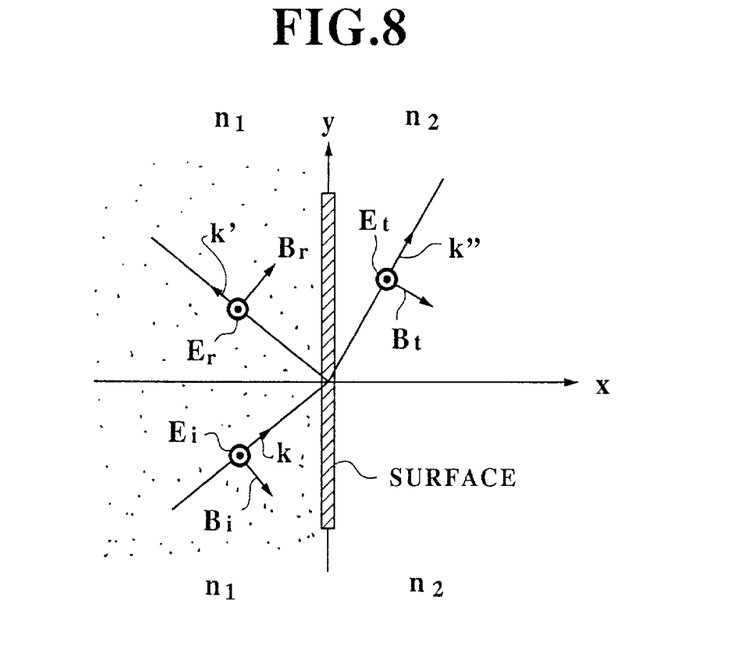
FIG. 8 is a vector graph showing transmission and reflection of the electromagnetic wave at a surface, where the y axis represents the surface between materials n1 and n2.
Figure 9:
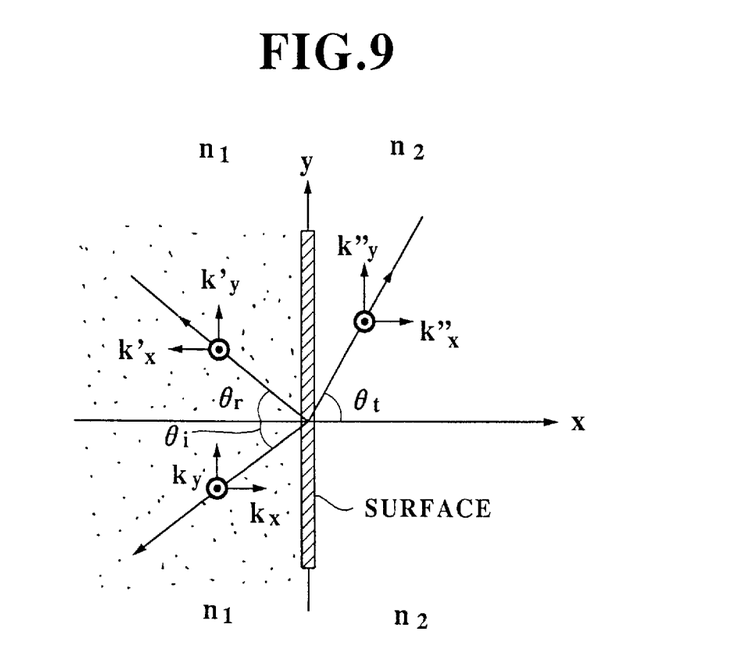
FIG. 9 is another vector graph showing the propagation vectors k, k' and k" for the incident, reflected and transmitted waves.
Figure 10:
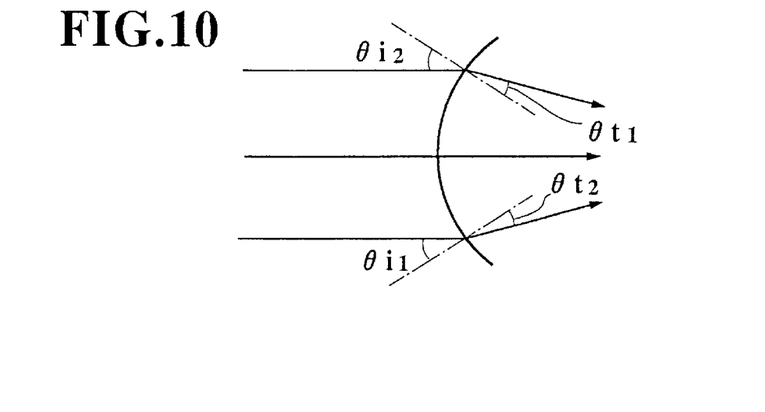
FIG. 10 illustrates divergence of the electromagnetic wave.
Figure 11:
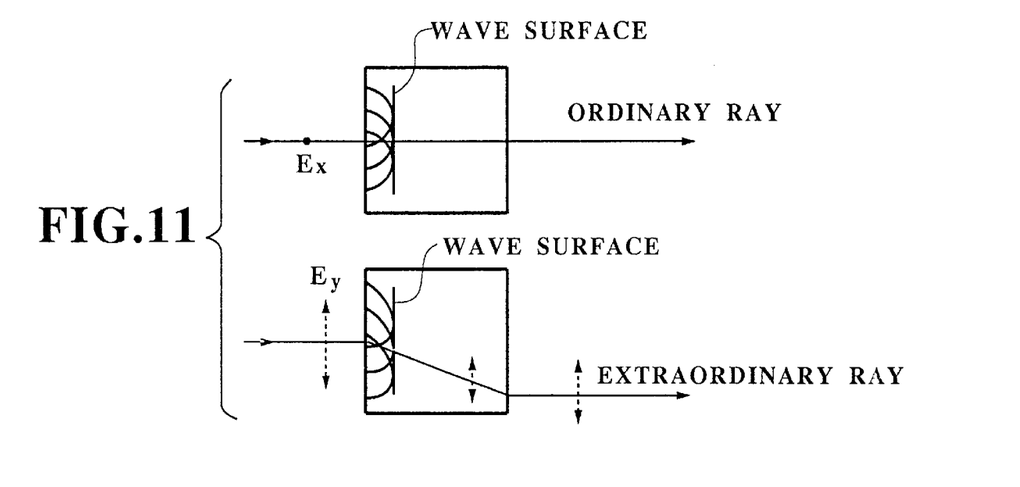
FIG. 11 illustrates birefringence of the electromagnetic wave.

Referring to FIG. 8 and FIG. 9, when the electromagnetic wave enters from material having refractive index n1 to another material having refractive index n2 with a boundary therebetween being x=0, there can be obtained the equations shown in FIG. 16-$t$ and FIG. 16-$u$ for the electric vector of the incident wave ($E_1$), the electric vector of the reflected wave $E_r$ and the electric vector of the transmitted wave $E_t$. In FIGS. 8 and 9, k, k', k" are propagation vectors for the incident, reflected and transmitted waves, respectively. In the same figures, there are illustrated different media n1 and n2 separated at the surface x=0 therebetween. It is to be noted that E is perpendicular to its propagation vector k for each wave.

Referring to FIGS. 8 and 9, notice that there is only the transmitted wave in region 2 (n2), while the fields in region 1 (n2) are the superposition of the fields of the incident and reflected waves. In other words, $$E_{1-E1}+E_r, E_2=E_t$$

and similarly for the B's.

Figure 16V:
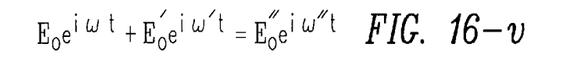
Figure 16W:
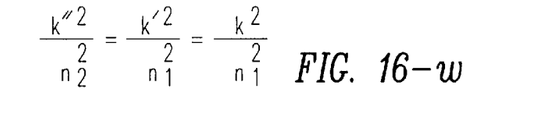
Figure 16X:
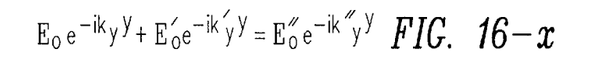

For the polarization, it is that $$E_1+E_r=E_t$$

at the boundary, that is, for x=0. Therefore, the equation shown in FIG. 16-$v$ must be true for all t and all y. When y=0, then the equation shown in FIG. 16-$w$ holds. This equation is interpreted that two oscillating terms are equal to a third oscillation, and that can happen only if all the oscillations have the same frequency. Therefore, $\omega''=\omega'=\omega$, where the frequencies of the reflected and transmitted waves are same with that of the incident wave.

By definition as given above, n=kc/ω thus k=nω/c, hence $k^2=n^2\omega^2/c^2$, so that there is obtained the equation shown in FIG. 16-$w$.

When t=0 is substituted at the equation shown in FIG. 16-$u$, there is obtained the equation shown in FIG. 16-$x$. Thereby, the equation shown in FIG. 16-$y$ is obtained. On the other hand, by $k'^2=k^2$ from the equation shown in FIG. 16-$w$, the equation shown in FIG. 16-$z$ is obtained.

Combining the equation shown in FIG. 16-$z$ with the equation shown in FIG. 16-$y$, there is obtained the equation shown in FIG. 16-$aa$. Now, since we are solving for one incident wave (notice also that the positive sign in the equation shown in FIG. 16-$aa$ makes no sense), we have the equation shown in FIG. 16-$ab$.

Figure 16Y:
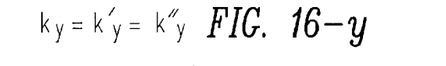
Figure 16Z:
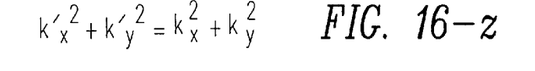

The equation shown in FIG. 16-$y$ and FIG. 16-$ab$ represent together that the angle of reflection θr is equal to the angle of incidence θi. The reflected wave is given by the equation shown in FIG. 16-$ac$.

For the transmitted wave, the equation shown in FIG. 16-$ad$ hold. Solving the equation shown in FIG. 16-$ad$, there is obtained the equation shown in FIG. 16-$ae$.

By the equation shown in FIG. 16-$ae$, since $k_x'' \geq k_x$ as n2 ≥ n1, θi≥θt. In this connection, for example, when the boundary between region 1 and region 2 is of a shape as shown in FIG. 7, the electromagnetic wave becomes convergent.

When a longitudinal axis of non-symmetric molecules is not parallel to a crystal plane, a birefringence occurs. In other words, with reference to FIG. 8, there is observed an extraordinary ray in addition to an ordinary ray. Moreover, in the material having the birefringence, the refractive index of the clockwise circularly polarized light may be considered different from that of the counterclockwise circularly polarized light. Thereby, by utilizing the material presenting a birefringence property, it may be possible that the convergence of the electromagnetic wave be further gained.

Moreover, when a member that has a close dielectric constant to that of material of a surface of the biological body is provided between the receiving coil and the biological body in a manner that such a member is preferably placed in contact with the biological body, the magnetic field $B_1$ (r) can be provided in a position orthogonal to the surface of the member. Thereby, the nonuniformity of imaging density caused by the boundary condition of the biological body under $B_1$ (r) of the receiving coil, can be maximally suppressed. Note that $B_1$ (r) represents a vector of RF magnetic wave of the receive coil (RF coil) in a point of the position vector r.

Accordingly, by utilizing the aqueous high-molecular gel sheet 4 shown in FIGS. 5–7, the inhomogeneity of the RF magnetic field especially inside the biological body can be significantly suppressed so that the nonuniformity of the imaging density in the MRI images can be avoided.

OPERATIVE ASPECT OF THE CONFIGURATION ACHIEVED BY THE PRESENT INVENTION

Let us describe below operation of the present invention in comparison and conjunction with the publication of Foo et al. SMRM abstracts, Vol. 1 pg. 510, Thomas K. F. Foo et al.; 1990.

It is to be noted that the imaging density nonuniformity in the MRI diagnostic apparatus becomes more noticeable as the magnitude of the static magnetic field becomes greater and as the Larmor frequency becomes higher. Therefore, by controlling in a manner that the wavelength of the biological body or the high-frequency (RF) magnetic field around the body is made longer, the imaging nonuniformity in the MRI image can be suppressed in the event that the magnitude of the static magnetic field is rather great.

For example, refer to report (SMRM 1990, annual meeting abstracts, p510) entitled "Manipulation of the Axial Propagation Constant by Dielectric Loading of the Coil-to-Shield Space to Improve RF Homogeneity" by Foo et al. In this report, by manipulating the axial propagation constant (wave number) $k_z$, i.e., by increasing the wavelength, the nonuniformity in sensitivity can be suppressed.

Hereinbelow, how to manipulate the propagation constant $k_z$ will be described.

Figure 1:
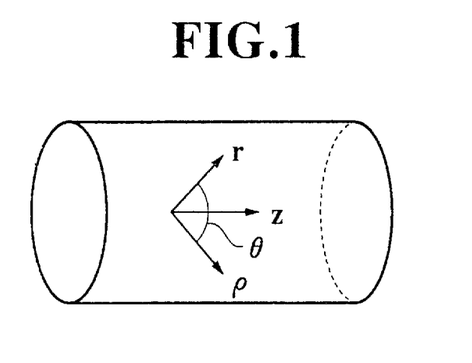
FIG. 1 illustrates a cylindrical coordinate system.

Referring to FIG. 1, a homogeneous cylindrical-shape body is exposed in the RF magnetic field expressed by the cylindrical coordinate system. When the body is disposed co-axially with the cylindrical coordinate system, the magnitude of RF magnetic field in the axial plane depends on the propagation constant $k_\rho$ which is the wave number in the r direction. In view of a boundary condition, there is obtained $$k\rho=k^2-k_z^2 \quad\text{---} \tag{A}$$

where k is the propagation constant inside the biological body and is given by following equation (B)

$$k^2=\omega_o^2\mu\epsilon j\omega o\mu\sigma \quad\text{---} \tag{B}$$

where ω indicates the Larmor frequency, $\mu$ is the magnetic permeability, $\epsilon$ is the dielectric constant, and σ is a conductivity of the body. It is to be noted that k corresponds to the propagation constant in the ρ direction shown in FIG. 1.

When the RF coil is surrounded by the air, $k_{z\sim ko}$. (where $k_o$ is the propagation constant in a vacuum atmosphere), and $K_o<<k, k_\rho$.

However, in Foo et al, the shield made of the copper film or the like (cylindrical shield) disposed inside the gantry is coated in the inner wall of the gradient coil, and inside the shield, there is a transmission coil. In this configuration, there is the disadvantage that spatial control is fixed in a position where the material is placed between the shield and the transmission coil. In other words, once the material is permanently filled in such a position, the available spatial control is limited, unlike in the present invention.

In contrast to the disadvantageous conventional practice, the operation of the MRI diagnostic apparatus according to the present invention will be described hereinbelow.

Here, if material having a large dielectric constant is placed in the vicinity of the RF coil, $k_z$ ($k_z \neq k_o$) can be increased. Thus, by equation (A), $k_\rho$ can be decreased, so that, equivalently, the propagation constant k inside body can be made small. Further, if the wavelength inside the body can be sufficiently long in comparison with the size of the body, the nonuniformity in contrast displayed in the MRI image can be mimimally suppressed.

Figure 2A:
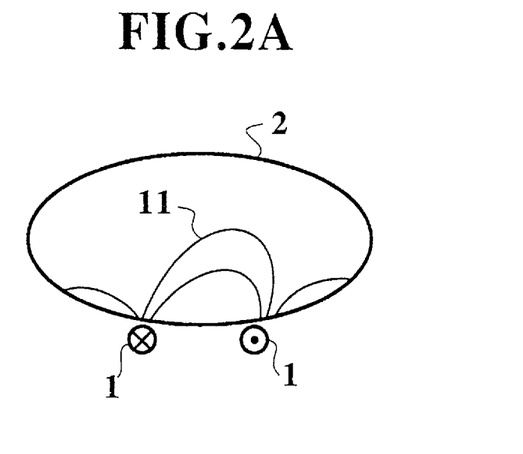
FIG. 2A and FIG. 2B illustrate a change in contour of signal intensity on an MRI image when there exists a biological body and when there does not exist the biological body, respectively.
Figure 2B:
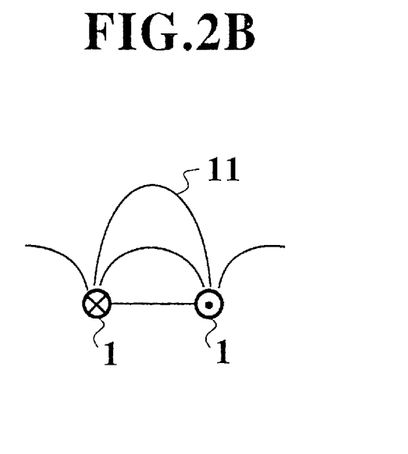

Moreover, if there exists nonuniformity in a spatial distribution $B_1$ (r) of the RF magnetic field produced by the transmitting and receiving coil, there occurs a static field in the longitudinal-axis direction of the body (z direction). Then, the image obtained in a plane orthogonal to the x-y plane, i. e., the tomographic image, may present an increased density nonuniformity. In other words, referring to FIG. 2B, a high-frequency magnetic equipotential line 11 produced by the surface coil 1 is of a symmetric distribution, when the biological body is not placed. On the other hand, referring to FIG. 2A, the high-frequency magnetic equipotential line 11 produced by the surface coil 1 may be distributed in a distorted manner when the biological body 2 is placed on the surface coil 1. Thereby, there is caused the density inhomogeneity in the tomographic image.

In a particular case where the receiving coil, such as the surface coil, has the nonuniformity in the spatial distribution $B_1$ (r) of the RF magnetic field, this density inhomogeneity occurs noticeably, for example, in a case where the Larmor frequency of a hydrogen nucleus is at a high frequency of 64 MHz under 1.5 Telsa. Telsa is a unit of magnetic field strength where 1 Telsa equals to 10,000 Gauss.

Figure 3:
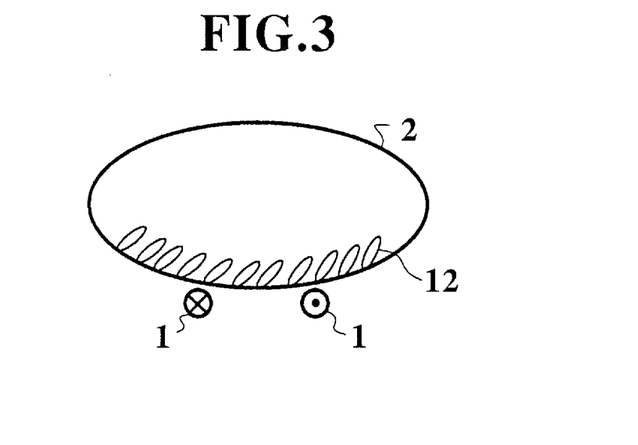
FIG. 3 illustrates a property of non-isotropic dielectric substance.

The above phenomenon may be caused by a shape of the body, thickness of a fat layer whose dielectric constant is great compared to other tissues, a distribution of a viscera whose conductivity is great compared to other tissues, and so on. In particular, the shape of the biological body constitutes a very important factor in order to present the boundary condition which determines how the spatial distribution $B_1$ (r) of the RF magnetic field produced by the receiving coil is propagated inside the body. Moreover, referring to FIG. 3, for example, when the body presents a property found in non-isotropic dielectric substances, e.g., when a molecule 12 is arranged as shown in FIG. 3, the index of refraction in the longitudinal axis (optical axis) of the molecule 12 differs from that in the minor axis of the molecule 12, that is vertical to the longitudinal axis, so that there is caused a birefringence.

For example, if an electric field distribution $D_1$ (r) associated with the RF magnetic field's spatial distribution $B_1$(r) is linearly polarized, the linearly polarized light is generally considered to be a wave overlapped in the x- and y-direction having same amplitude and phase respectively. Thus, if the direction of the polarized light has, for example, a gradient of 45° with respect to the optical axis, the speeds of the polarized light in the x- and y-directions differ, so that the phases therefor differ. The dislocation amount varies in accordance with the thickness of the non-isotropic material (here it is assumed that the non-isotropic material is evenly present at a predetermined thickness). In other words, when its thickness is such that the phase difference of the polarized light in the x- and y-directions is 90°, the linearly polarized light becomes circularly polarized light.

Figure 4:
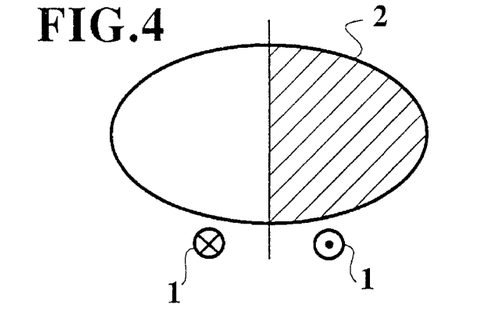
FIG. 4 illustrates a sectional view for use in explanation of a state where the propagation of the magnetic line of force differs between in a right side and a left side of the biological body whose longitudinal-axis direction is placed in the same direction as the static magnetic field.

Thereby, referring to FIG. 4, propagation of electric field $D_1$ (r) as well as the propagation of RF magnetic field $B_1$ (r) may not be symmetric in the right side and left side of the biological body.

In view of the above, in the present invention, there is provided a material, disposed in the vicinity of the RF coil, where the material has a high dielectric constant (relative permittivity). Such a material has flexibility and has the easily deformable characteristic as a sheet of paper. Thereby, the material (serving as matching layer) can be mounted around or in contact with the biological body. Or, the material may be provided on the RF coil itself.

Then, finally obtained image quality in the MRI diagnostic apparatus may deteriorate unless the magnitude of a dielectric loss and magnetic loss of the RF coil caused by the material that is provided in the vicinity of the RF coil, is sufficiently small relative to that of the dielectric loss and magnetic loss of the biological body when the RF coil is provided in place without the material being provided. The reason therefor is that since a Q value of the RF coil is decreased then, overall transmitting and receiving efficiency is deteriorated. The Q value is the ratio of stored energy to mean energy dissipation per cycle.

Accordingly, the distribution of the RF magnetic field inside the biological body can be optimally controlled by providing aqueous high-molecular gel material in a part of or around the entire RF coil or the biological body.

In general, even in a poly ion complex (especially one including water content) to which an acid high-molecular electrolyte and a basic high-molecular electrolyte are mixed in a same amount, there occurs a local cluster of a dissociated group and the water content. Then, the dissociated ion moves within this cluster, so that a great deal of permittivity (dielectric constant) and dielectric loss may be observed. Moreover, since a glass transition point is decreased due to the water content in the aqueous high molecule, the permittivity due to the ion is said to increase significantly as the water content increases.

Accordingly, the permittivity or conductivity for the aqueous high molecule may be significantly increased compared to a usual monomolecular material. Especially when this aqueous high-molecular gel is used in the RF magnetic field which presents a Larmor frequency having a unit of some meters of the wavelength in the MRI diagnostic apparatus where the density inhomogeneity is significant and a strong magnetic field is present, the RF magnetic field equivalent to a medium or weak magnetic field whereby the density inhomogeneity is minimally suppressed can be applied to the biological body Besides those already mentioned above, many modifications and variations of the above embodiments may be made without departing from the novel and advantageous features of the present invention. Accordingly, all such modifications and variations are intended to be included within the scope of the appended claims.

What is claimed is:

1. A magnetic resonance imaging (MRI) diagnostic apparatus for applying a radiofrequency (RF) pulse to a biological body, and for acquiring nuclear magnetic resonance (NMR) signals therefrom to be reconstructed to obtain an MRI image, the apparatus comprising:

an RF coil for applying the RF pulse directed to the biological body; and a field correcting means of a sheet material filled with a high molecular gel with a dielectric constant greater than 30 and having a magnetic susceptibility approximately within +150% of the biological body, said sheet material interposed between the RF coil and a position where the biological body is to be placed, said sheet material of a deformable material, and having a contact surface, capable of supporting the biological body to create a contiguous and direct contact between the contact surface and the biological body, and for correcting a distribution of an RF magnetic field at the time of RF transmitting or receiving by the RF coil.

2. The apparatus of claim 1, wherein the field correcting means changes a phase of the RF magnetic field.

3. The apparatus of claim 1, wherein the field correcting means is provided on a part of or around the entire RF coil.

4. The apparatus of claim 1, wherein the field correcting means includes a heat dissipation means for dissipating heat applied to the biological body caused by the applied RF pulse thereto.

5. The apparatus of claim 1, wherein the sheet material filled with the high-molecular gel contains a water content therein.

* * * * *